United States Patent [19]

Walter

[11] Patent Number: 4,490,535

[45] Date of Patent: Dec. 25, 1984

[54] 4-(3- AND 4-CHLOROCYCLOHEX-3-ENYL)PYRIDINE INTERMEDIATES

[75] Inventor: Thomas J. Walter, Baton Rouge, La.

[73] Assignee: Ethyl Corporation, Richmond, Va.

[21] Appl. No.: 479,259

[22] Filed: Jun. 20, 1983

Related U.S. Application Data

[62] Division of Ser. No. 300,046, Sep. 8, 1981, Pat. No. 4,405,792.

[51] Int. Cl.$^3$ .......................................... C07D 213/26
[52] U.S. Cl. .................................... 546/346; 546/350
[58] Field of Search ........................................ 546/346

[56] References Cited

U.S. PATENT DOCUMENTS 3,753,993  8/1973  Lesher et al. ...................... 546/156
3,907,808  9/1975  Lesher et al. ...................... 546/156

*Primary Examiner*—Alan L. Rotman
*Attorney, Agent, or Firm*—Donald L. Johnson; John F. Sieberth; Patricia J. Hogan

[57] ABSTRACT

4-(3- and 4-chlorocyclohex-3-enyl)pyridines, useful as intermediates in the preparation of pesticides and bactericides, are prepared by reacting a 4-vinylpyridine with chloroprene.

3 Claims, No Drawings

4-(3- AND 4-CHLOROCYCLOHEX-3-ENYL)PYRIDINE INTERMEDIATES

This application is a division of application Ser. No. 300,046, filed Sept. 8, 1981, now U.S. Pat. No. 4,405,792 issued Sept. 20, 1983.

This invention relates to the preparation of 4-(3- or 4-halophenyl)pyridines and to novel intermediates for the synthesis of such compounds.

BACKGROUND

A three-step synthesis of 4-phenyl pyridine from alphamethyl styrene, formaldehyde and ammonium chloride has been reported by Schmidle and Mansfield, J. Am. Chem. Soc., 78, 1702–1705 (1956). In that process the reactants are condensed to form 6-methyl-6-phenyl-tetrahydro-1,3-oxazine. This is converted with excess acid to 4-phenyl-1,2,3,6-tetrahydropyridine which in turn is dehydrogenated to 4-phenyl pyridine using nitrobenzene and palladium catalyst. The authors point out both in the foregoing paper and in U.S. Pat. No. 2,847,414 that this dehydrogenation reaction can be effected in the presence or absence of a hydrogen acceptor such as nitrobenzene. The patent indicates that the dehydrogenation should be conducted at temperatures between 125° and 220° C.

The condensation of 4-vinyl pyridine with diene hydrocarbons has been described by Petrov and Lyudvig, The Journal of General Chemistry of the U.S.S.R., Volume 26, January 1956 (English Translation Copyright 1956), Consultants Bureau, Inc., New York, N.Y., pages 49–51. The authors investigated the reaction of 4-vinyl pyridine with butadiene, piperylene, isoprene, diisopropenyl and cyclopentadiene. All the substances, apart from that prepared from cyclopentadiene, were subjected to dehydrogenation over palladium. The resultant arylpyridines were isolated in the form of picrates.

The use of chloroprene in Diels-Alder reactions with acrylic acid or styrene is reported by Titov and Kuznetsova, Bulletin of the Academy of Sciences USSR, Division of Chemical Sciences (English Translation, 1960, page 1687).

In order to synthesize halophenylpyridines, previous workers have resorted to reactions between a diazonium salt and a pyridine. See in this connection Butterworth, Heilborn and Hey, J. Chem. Soc., 1940, 355–358 and Netherlands Application No. 6,414,307, June 11, 1965 [Chemical Abstracts, 64 713d (1966)]. In these procedures, mixed isomers are formed and thus in order to recover the individual isomers in relatively pure form, recourse was had to such separation techniques as fractional crystallization and column chromatography.

It is known that aryl halogen atoms can be removed by hydrogen in the presence of a noble metal catalyst such as palladium. See H. O. House, *Modern Synthetic Reactions*, 2nd Edition, W. A. Benjamin Publishers, Copyright 1972, page 14.

THE INVENTION

It has now been found that:
(a) Novel compounds, viz., 4-(3- or 4-chlorocyclohex-3-enyl)pyridines, can be prepared by reacting a 4-vinyl pyridine with chloroprene under conditions whereby a Diels-Alder-type condensation occurs; and (b) 4-(3- or 4-chlorophenyl)pyridines can be prepared by catalytically dehydrogenating a 4-(3- or 4-chlorocyclohex-3-enyl)pyridine in the presence of a suitable hydrogen acceptor.

Thus, in accordance with one embodiment of this invention there is provided a process for the preparation of 4-chlorophenyl)-pyridines in which the chlorine atom is in the 3- or 4-position of the phenyl group which comprises reacting a 4-vinyl pyridine with chloroprene to form a 4-(3- or 4-chlorocyclohex-3-eenyl)-pyridine (usually a mixture of these isomers is formed) and then catalytically dehydrogenating the 4-(3- or 4-chlorocyclohex-3-enyl)-pyridine to form a 4-(3- or 4-chlorophenyl)pyridine. Preferably a mixture of 4-(3-chlorocyclohex-3-enyl)pyridine and 4-(4-chlorocyclohex-3-enyl)pyridine is subjected to this catalytic dehydrogenation. It is possible, however, to separate these isomers, for example by selective crystallization techniques or the like, and thereupon subject either isomer to the catalytic dehydrogenation.

The reactions of this invention may be depicted as follows:

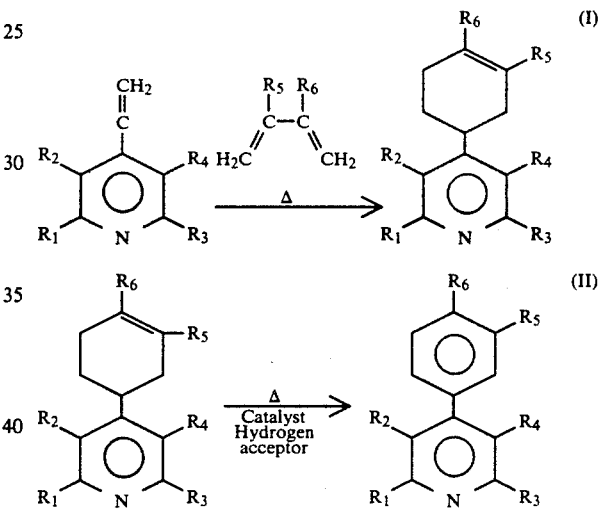

In these equations $R_1$, $R_2$, $R_3$ and $R_4$ are, independently, hydrogen or innocuous substituents, and one of $R_5$ and $R_6$ is chlorine and the other is hydrogen. Exemplary innocuous substituents, i.e., substituents which ordinarily do not prevent the designated reaction from taking place nor promote excessive decomposition of the desired product include lower alkyl, aryl, aralkyl, cycloalkyl, haloalkyl, haloaryl, ring-haloaralkyl, alkoxy and aryloxy, halo substituents (i.e., fluoro, chloro and bromo), nitrogen containing heterocyclic groups, and the like.

Other embodiments of this invention include the condensation process itself, the novel products formed in the condensation process, and the dehydrogenation process itself. These and other embodiments of the invention will be still futher apparent from the ensuing description and appended claims.

CONDENSATION PROCESS

Reaction temperatures in the range of about 50° to about 250° C. and preferably in the range of about 100° to about 150° C. are recommended.

Although it is possible to conduct the reaction in the absence of an added solvent, it is preferable to use a reaction diluent. Among the solvents which may be used for this process are aromatic hydrocarbons, paraffinic hydrocarbons, cycloparaffinic hydrocarbons, aliphatic halohydrocarbons, aromatic halohydrocarbons, ethers, esters and the like. Naturally, the solvent selected should exist in the liquid state at the reaction temperature employed.

The proportions as between the 4-vinyl pyridine reactant and the chloroprene can be varied to a considerable extent. Ordinarily, it will be found desirable to employ the reactants in a molar ratio (chloroprene:4-vinyl pyridine reactant) in the range of from about 0.5:1 up to about 10:1 and preferably in the range of about 0.75:1 to about 2:1.

The condensation reaction is not particularly rapid and accordingly reaction periods ranging from about 0.25 to about 20 hours are generally found most satisfactory.

For best results, the reaction should be performed in a closed reaction system such as a pressure-resistant autoclave. Desirably, the reaction should be performed under an inert atmosphere so as to minimize the side reactions such as polymerization and the like. In order to further minimize polymer formation, it is possible to introduce either or both of the reactants into the heated reaction system on an incremental basis. Polymerization inhibitors such as phenothiazine, oxygen, phenolic or aromatic amino compounds and the like may be added. In this way, the desired Diels-Alder-type condensation reaction in favored-over competitive polymerization reactions.

This condensation process gives rise to the formation of novel products, viz., 4-(chlorocyclohex-3-enyl)pyridines of the formula

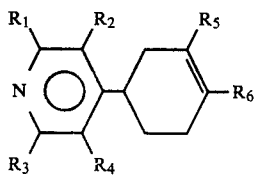

wherein $R_1$, $R_2$, $R_3$ and $R_4$ are, independently, hydrogen, or innocuous substituents (see above) and wherein one of $R_5$ and $R_6$ is chlorine and the other is hydrogen.

To recover these products from the reaction mixture, it may be desirable to utilize extraction procedures rather than distillation. For example, use of aqueous acidic extraction procedures such as set forth in the examples hereinafter enables isolation of the pyridine derivatives from the balance of the reaction mixture. Other workup procedures may prove useful such as fractional crystallization, column chromatography, and the like. The isolated products may be further purified by distillation.

As noted above—see Equation (I)—the process is applicable to a variety of suitably substituted 4-vinyl pyridines. Illustrative compounds for use in this reaction include 2-methyl-4-vinylpyridine, 2,3-dimethyl-4-vinylpyridine, 3-ethyl-4-vinylpyridine, 2,3,5,6-tetramethyl-4-vinylpyridine, 2-phenyl-4-vinylpyridine, 2-(2-pyridyl)-4-vinylpyridine, 2-chloro-4-vinylpyridine, 3-trifluoromethyl-4-vinylpyridine, 3,5-diethoxy-4-vinylpyridine, 2-(2-tetrahydrofuranyl)4-vinylpyridine, and the like.

Use of 4-vinyl pyridine itself is most preferred pursuant to this invention.

DEHYDROGENATION PROCESS

In this process, 4-(chlorophenyl)pyridines in which the chlorine is in the 3- or 4-position are produced by heating 4-(3- or 4-chlorocyclohex-3-enyl)pyridine with a dehydrogenation catalyst in the process of a hydrogen acceptor to a dehydrogenation temperature so that the desired product is formed. A feature of the process is that the cyclohexenyl ring is aromatized without concommitant loss of chlorine from the chlorophenyl product.

As noted above, it is preferred to employ a mixture of 4-(3-chlorocyclohex-3-enyl)pyridine and 4-(4-chlorocyclohex-3-enyl)-pyridine in this process as this enables use of the mixed isomer product as formed in the condensation process. When using such mixtures, the resultant 4-(chlorophenyl)pyridine will be a mixture of the 3-chlorophenyl and 4-chlorophenyl isomers. However, the aromatization process of this invention may be applied to either of the above-individual 4-(chlorocyclohex-3-enyl)pyridine isomers, i.e., the 3-chloro isomer or the 4-chloro isomer.

The catalyst used in the process is preferably a palladium catalyst. The catalyst may be employed in various physical forms, for example, it may be supported on alumina or other suitable carrier. A catalyst composed of palladium on carbon has been found particularly useful in the process. Normally, the catalyst will be used in particulate or subdivided form. Quantities ranging from about 0.1 to about 50 weight percent—preferably 1 to 10 weight percent—based on the weight of the 4-(chlorocyclohex-3-enyl)pyridine being aromatized are generally used although departures from these ranges are permissible.

Hydrogen acceptors suitable for use in the process include dinitrobenzenes; nitroalkanes such as nitroethane; alkenes such as ethylene and propylene; substituted quinones; and the like. Nitrobenzene and its congeners are preferred for use in the process. For best results, the hydrogen acceptor should be in the liquid phase in the reaction system under the reaction conditions being employed.

The relative proportions as between the 4-(3- or 4-chlorocyclohex-3-enyl)pyridine and the hydrogen acceptor can be varied to a considerable extent, provided of course, there is a sufficient amount of the hydrogen acceptor to perform its desired function in the reaction system. Ordinarily, enough hydrogen acceptor is added to absorb all of the hydrogen from the aromatization. A particularly convenient method of operation is to use the hydrogen acceptor as the solvent and thus very substantial excesses may be used.

Exemplary 4-(chlorocyclohex-3-enyl)pyridines for use in this process include 4-(4-chlorocyclohex-3-enyl)-3-methylpyridine, 4-(4-chlorocyclohex-3-enyl)-2-propoxypyridine, 4-(3-chlorocyclohex-3enyl)-2-(4-tolyl)pyridine, 4-(4-chlorocyclohex-3-enyl)-2,6-dimethylpyridine, 4-(3-chlorocyclohex-3-enyl)-2-6-dichloropyridine, and the like. Particularly preferred are 4-(4-chlorocyclohex-3-enyl)pyridine and 4-(3-chlorocyclohex-3-enyl)pyridine, and mixtures thereof.

Reaction temperatures generally fall within the range of about 100° to about 300° C. and are selected in any given case to achieve a suitable rate of dehydrogenation without incurring an undesired amount of dechlorination. In short, the dehydrogenation temperature employed is one at which the 4-(3- or 4-chlorocyclohex-3- enyl)pyridine is dehydrogenated so that a 4-(3- or 4-chlorophenyl)pyridine is formed.

The 4-(3- or 4-chlorocyclohex-3-enyl)pyridine, dehydrogenation catalyst, and hydrogen acceptor should be heated in contact with each other for a sufficiently long period for the desired aromatization to take place. Reaction periods ranging from about 0.25 to about 40 hours are generally most satisfactory although, of course, the length of the reaction period may be affected to some extent by the quantity and activity of the catalyst and by the reaction temperature being employed.

If desired, the reaction mixture may include an inert solvent or diluent.

Workup procedures involving extraction techniques, fractional crystallization, distillation and column chromatography have been found useful.

The practice of this invention will be still further apparent from the following illustrative examples.

EXAMPLE I

A stainless steel bomb was charged with a performed mixture of 30 g (286 mmoles) of 4-vinyl pyridine, 76 g of a 50 percent chloroprene solution [i.e., 37.9 g (429 mmoles) of chloroprene], 15 ml of xylene, and 0.33 g (1.4 mmoles) of 2,6-di-tert-butyl-p-cresol antioxidant. The reaction mixture was heated by means of an oil bath at 150°–160° C. for ten hours. The pressure within the sealed bomb remained below 100 psi. After ten hours, the contents of the bomb were gradually allowed to cool to room temperature. The reaction mixture, a rather thick slurry of tan colored material, was removed from the bomb by means of methylene chloride. A portion of the resultant mixture was extracted with aqueous HCl, followed by neutralization. Analysis of the resultant oil by gas chromatography and NMR spectroscopy showed that most of the vinyl pyridine was consumed and that three major new products were formed, presumably including 4-(3- and 4-chlorocyclohex-3-enyl)pyridines.

EXAMPLE II

A mixture of 4-vinyl pyridine (20 g) and chloroprene (20 ml of a 50 weight percent solution in xylene) was heated in a sealed tube equipped with a pressure gauge for 20 hours at 160°–165° C. No significant pressure change occurred—the pressure rose by about 20 psi. At the end of the 20-hour reaction period, the reaction mixture, which initially contained the reactants in a molar ratio of 1:2 (chloroprene to 4-vinyl pyridine), was transferred to a separatory funnel and extracted three times with 1N HCl (50 ml portions). The organic layer was discarded. The aqueous layer was then treated with 50 percent aqueous sodium hydroxide solution until the pH was approximately 10. This mixture was then extracted with methylene chloride three times (50 ml portions) and the combined methylene chloride layers dried with potassium carbonate. The dried methylene chloride mixture was then filtered and the filtrate was quickly evaporated using a rotary evaporator followed by a vacuum pump leaving about 13 g of an oily residue. Analysis by gas chromatography indicated the presence of only two major products. This oily residue was taken up in diethyl ether yielding a milky solution from which a whitish precipitate settled. The ether layer was collected and evaporated to give approximately 10 g of an oily product which still contained two major products as indicated by gas chromatography. The residue was distilled at 15 mm pressure at about 60°–65° C. to remove any residual 4-vinyl pyridine. The residue was further distilled at 110°–120° C. at 0.3 mm pressure yielding two fractions, the first of which (approximately 3 g) contained the two major products. This fraction was separated into two products by means of thin layer chromatography using silica gel and diethyl ether solvent. NMR spectoscopy indicated that one of these products was probably a dimer of 4-vinyl pyridine. The other product, the major component in the system, was identified to be a mixture of 4-(3- and 4-chlorocyclohex-3-enyl)-pyridines with the assistance of carbon and proton NMR spectroscopy.

EXAMPLE III

A mixture of 170 mg of the 4-(3- and 4-chlorocyclohex-3-enyl)pyridines produced in Example II, 20 mg of 5 percent palladium on carbon, and one ml of nitrobenzene was stirred under nitrogen for three hours at 120° C. High pressure liquid chromatography indicated that no appreciable reaction had occurred under these conditions. Thus, the same reaction mixture was heated to 225° C. and the refluxing mixture maintained under nitrogen. Periodic inspection of the reaction mixture by means of high pressure liquid chromatography showed that by the end of six hours a significant quantity of 4-(chlorophenyl)pyridines had been formed. In this six hour reaction period, the reaction proceeded to about 80 percent completion. After cooling to room temperature, the crude reaction mixture was partitioned between chloroform (50 ml) and 1N HCl and the chloroform layer extracted several times with 1N HCl. The darkly colored combined aqueous layer was treated with a small quantity of activated charcoal, heated with stirring for ten minutes and filtered. The filtrate, no longer dark in color, was neutralized with sodium hydroxide to a pH of about 10 and again extracted with chloroform several times. The chloroform layers were combined, dried and evaporated to give 15 mg of a black residue. This residue was taken in a small amount of methanol and the methanol solution subjected to high pressure liquid chromatography which indicated the presence of 4-(3- and 4-chlorophenyl)pyridine. Identification was assisted by comparison with 4-(4-chlorophenyl)pyridine prepared by an independent route.

EXAMPLE IV

A mixture of 200 mg of 4-(3- and 4-chlorocyclohex-3-enyl)pyridines prepared in Example II, 30 mg of 5 percent palladium on carbon, and one ml of acetophenone was heated at 225° C. for four hours under nitrogen atmosphere. High pressure liquid chromatography showed that no product had been formed under these conditions, thus indicating acetophenone is not an efficient hydrogen acceptor for use in the process. Thereupon, about 0.5 ml of nitrobenzene was added to this mixture and then heating continued at 225° C. Shortly thereafter, the process was found by means of high pressure liquid chromatography to have proceeded to about 50 percent completion with the resultant formation of 4-(3- and 4-chlorophenyl)pyridines along with other by-products.

EXAMPLE V

A mixture of 4-vinyl pyridine (5 ml) and chloroprene (15 ml of a 50 percent by weight solution in xylene) was heated in a sealed polytetrafluoroethylene reactor (20 ml capacity) for ten hours at 125°–130° C. In this reaction the initial molar ratio was about 1.6:1 (chloroprene:4-vinyl pyridine). The resultant reaction mixture was yellowish in color and contained some solid materials. Unreacted 4-vinyl pyridine and chloroprene, and xylene solvent were evaporated off, and the residue taken up in methanol and filtered. The filtrate was again evaporated yielding a reddish oil which was taken up in methylene chloride and extracted three times with 2N HCl (100 ml portions). The combined HCl washings were shaken thoroughly with three separate portions of diethyl ether (50 ml each) and the HCl layer was then neutralized with sodium hydroxide to a pH of about 12. A dark color product separated and this was extracted with methylene chloride. Evaporation of the methylene chloride left a reddish liquid which after pumping on a vacuum pump gave 3.5 g of a crude product. NMR spectra indicated that the major components in this product were the 4- (3- and 4-chlorocyclohex-3-enyl)-pyridines.

EXAMPLE VI

By refluxing 150 mg of 4-(3- and 4-chlorocyclohex-3-enyl)-pyridines produced in Example II with 10 mg of 5 percent palladium on carbon in nitrobenzene at 225° C. for 5 hours, the reaction was shown by high pressure liquid chromatography (HPLC) to have gone to 50 percent completion. The nitrobenzene was removed by steam distillation, the residue was partitioned between methylene chloride and water, and the organic layer was dried and evaporated to give a darkly colored product containing 4-(3- and 4-chlorophenyl)pyridines.

EXAMPLE VII

A mixture of 80 mg of 4-(3- and 4-chlorocyclohex-3-enyl)-pyridines produced in Example II, one ml of nitrobenzene and 20 mg of 5 percent palladium on carbon was refluxed at 145°-150° C. and 80 mm pressure for 4 hours. HPLC indicated no reaction had occurred under these conditions. By heating the mixture at 170°-180° C. at atmospheric pressure overnight, a small conversion (less than 10 percent) to the desired 4-(3- and 4-chlorophenyl)-pyridine product occurred.

EXAMPLE VIII

A condensation reaction was performed by heating 2.5 ml of 4-vinyl pyridine, 10 ml of chloroprene and 50 mg of 2,6-di-tert-butyl-p-cresol antioxidant at 125°-130° C. for 10 hours. The liquid reaction product, which contained a ball of rubbery polymer, was taken up in methanol. Evaporation of the methanol left an oily residue. This was taken up in diethyl ether and extracted three times with 6N HCl (total 100 ml). The aqueous layer was neutralized with aqueous sodium bicarbonate to pH 7. The product was then extracted three times with chloroform (100 ml portions). The chloroform solutions were combined, dried and evaporated to give 1.3 g of an oil which was indicated by gas chromatography to contain only two products, viz., the desired 4-(3- and 4-chlorocyclohex-3-enyl)pyridines in the ratio of 76:24, respectively.

EXAMPLE IX

A mixture of 130 mg of the 4-(3- and 4-chlorocyclohex-3-enyl)pyridine produced in Example II, 50 mg of acetic acid, 10 mg of 5 percent palladium on carbon and one ml of nitrobenzene was stirred for 4 hours at 120° C. High pressure liquid chromatography revealed that no reaction had occurred to this point. Then the mixture was heated at 190° C. and 150 mm pressure for 6 hours. HPLC indicated that to this point only a small conversion (about 2 percent) to the desired product had taken place. Thereupon, the mixture was heated at 225° C. at atmospheric pressure for 8 hours. The HPLC analysis of this crude reaction product showed it to be a 50:50 mixture of starting material and reaction products. The crude reaction mixture was taken in ether and solids filtered off. The ether solution was extracted three times with 50 ml portions of 1N HCl. The aqueous layers were combined, washed twice with ether (50 ml portions), neutralized with aqueous KOH to pH of about 10, and extracted with ether. The ether solution was then dried, filtered and evaporated to give about 100 mg of a reddish oil containing, inter alia, the desired 4-(3- and 4-chlorophenyl)-pyridines.

EXAMPLE X

A mixture of 1.5 ml of 4-vinyl pyridine, 6 ml of a 50 percent by weight solution of chloroprene in xylene, 12 ml of xylene and 30 mg of 2,6-di-tert-butyl-p-cresol antioxidant was heated at 125°-130° C. in a sealed polytetrafluoroethylene reactor for 10 hours. The reaction mixture was taken up in ether and extracted with 6N HCl (3 times; 20 ml portions) to give a pale yellowish aqueous layer. This layer was further washed with ether and then neutralized with aqueous potassium hydroxide solution to pH 8. This was then extracted with chloroform (4 times; about 100 ml portions). The organic layer was cloudy and was again washed with water and then with saturated saline solution, dried and evaporated to give about 1.2 g of an oily product. Analysis by gas chromatography showed that the major product was the desired 4-(3- and 4-chlorocyclohex-3-enyl)pyridines, together with unreacted starting materials. Volatiles were stripped from this oily product by means of a vacuum pump yielding as residue 0.7 g of a reddish orange oil, which consisted mostly of the desired product (i.e., the foregoing two chlorocyclohex-3-enyl isomers). The yield of this product was estimated to be about 30–40 percent based on the amount of stirring material used and the purity of the product as indicated by gas chromatography.

EXAMPLE XI

A reaction mixture composed of 100 mg of 4-(3- and 4-chlorocyclohex-3-enyl)pyridines, 10 mg of 5 percent palladium on carbon and 2 ml of dodecene was heated under a nitrogen atmosphere at 240° C. for 6 hours. This gave only a 2 percent conversion to the desired product based on HPLC analysis.

EXAMPLE XII

A mixture of 210 mg of 4-(3- and 4-chlorocyclohex-3-enyl)-pyridine, 20 mg of 5 percent palladium on carbon and 2 ml of nitrobenzene was refluxed for 8 hours at 240° C. under a nitrogen atmosphere. HPLC showed that under these conditions all of the starting material had reacted and thus the conversion to reaction product was at least 98 percent. The crude mixture was taken up in ether, extracted with 1N HCl (3 extractions; 50 ml each) and the aqueous layer neutralized with aqueous KOH solution. The organic phase was again extracted with ether (3 times; 50 ml each) and the combined layers dried with potassium carbonate overnight. Evaporation of the ether layer gave a reddish orange oil, which when taken up in hexane and treated with a small quantity of activated charcoal, became a pale yellow oil. The NMR spectrum of this product showed it to contain the desired 4-(3- and 4-chlorophenyl)pyridines, together with unreacted starting material.

EXAMPLE XIII

Heated at 130°–140° C. for 10 hours was a mixture of 1.5 ml of 4-vinyl pyridine, 6 ml of 50 percent by weight solution of chlorophene in xylene, 12 ml of xylenes and 150 mg of 2,6-di-tert-butyl-p-cresol antioxidant. The crude reaction mixture was taken up in ether (100 ml) and extracted with 1N HCl (4 times; 50 ml portions). The HCl layer was then neutralized with aqueous KOH to a pH of about 10 and extracted with chloroform. The chloroform layer was dried, filtered and evaporated under reduced pressure to give an oily product which contained, in addition to unreacted starting materials and dimer from 4-vinyl pyridine, a quantity of the desired 4-(3- and 4-chlorocyclohex-3-enyl)pyridines. The ratio of this desired product to the dimer was about 7:1.

EXAMPLE XIV

Several crude product mixtures from condensation reactions reported in earlier examples herein were combined and distilled at 150°–160° C. (reflux temperature) at low pressure (0.5–0.3 mm). The fraction collected at these temperatures contained 4-(3- and 4-chlorocyclohex-3-enyl)pyridines of a purity of at least about 80 percent as shown by gas chromatography. A portion of this distillation (550 mg) was heated with 90 mg of 5 percent palladium on carbon in 5 ml of nitrobenzene for 8 hours at 240° C. The reaction mixture was taken up in methanol (about 5 ml) and this solution was slowly added to 100 ml of ether. The ether layer was filtered, the filtrate was extracted 4 times with 1N HCl (50 ml portions) and then the aqueous layer was washed 3 times with ether (100 ml portions). The aqueous layer was then neutralized to a pH of about 9 and again extracted with ether. The ether layer was dried, filtered and then evaporated to give about 420 mg of product. HPLC indicated that this contained a substantial quantity of the desired 4-(3- and 4-chlorophenyl)pyridines. This mixture was taken up in hexane and treated with activated charcoal. After heating the mixture to reflux, it was then filtered and the filtrate was evaporated to give 200 mg of an oil which was shown by NMR spectroscopy to be a mixture of the desired 4-(3- and 4-chlorophenyl)pyridines, together with unreacted starting material. The yield of this product was estimated from spectral data to be about 20 to about 25 percent.

EXAMPLE XV

A condensation reaction was performed using 1.5 ml of 4-vinyl pyridine, 6 ml of chloroprene (50 percent solution in xylene), 12 ml of xylene and 150 mg of 2,6-di-tert-butyl-p-cresol antioxidant. The reaction conditions involved heating for 6 hours at 120°–130° C. Analysis of the crude reaction mixture indicated that extensive reaction had not occurred under these conditions. Nevertheless, the crude reaction mixture was taken up in ether and extracted with 1N HCl (3 times; 50 ml portions). Then the aqueous layer was washed with 50 ml portions of ether, neutralized with KOH and extracted with chloroform (3 times; 50 ml portions). The chloroform layer was dried, filtered and evaporated yielding about 0.7 g of an oil which contained mostly unreacted starting materials. On further evaporation, the starting materials were stripped off leaving about 220 mg of an almost colorless oil which contained the desired 4-(3- and 4-chlorocyclohex-3-enyl)pyridines and a dimer from 4-vinyl pyridine in a ratio of 9:1. The conversion in this case was only about 10 percent.

EXAMPLE XVI

A pressure bottle was charged with 10.5 ml of 4-vinyl pyridine, 42 ml of chloroprene, 84 ml of xylene solvent and 210 mg of 2,6-di-tert-butyl-p-cresol antioxidant. This mixture was heated in the sealed bottle for 5 hours at 180°–190° C. The product formed under these conditions had an excessive rubbery consistency thus indicating that extensive polymerization had occurred (the initial chloroprene to 4-vinyl pyridine molar ratio was 2:1).

EXAMPLE XVII

A sample of 4-(3- and 4-chlorocyclohex-3-enyl)pyridine of a purity greater than 93 percent, together with 40 mg of 5 percent palladium on carbon and 5 ml of nitrobenzene was heated under reflux for 15 hours at 230°–240° C. At the end of this time the HPLC trace showed that the reaction was essentially complete. The reaction mixture was poured into 100 ml of anhydrous ether and the ether solution was filtered. The filtrate was extracted 4 times with 1N HCl solution (50 ml portions). The combined aqueous layer was washed twice with 50 ml portions of ether and neutralized to pH 10 with sodium hydroxide solution (50 percent). The product was then extracted several times with hexane and the hexane layers were combined, dried, treated with a small quantity of activated charcoal, and filtered. The treated product (approximately 170 mg) was chromatographed on a 2 mm silica gel plate and eluted with diethyl ether. This chromatographic procedure was repeated 4 times. The major band, identified by shining UV light on the plate, was isolated and the organic material extracted therefrom with a mixture of 5 percent methanol in chloroform. The chloroform layer was evaporated yielding about 127 mg of an oily product. Analysis by gas chromatography showed 3 peaks and NMR established the presence of the desired product. A mass spectrum revealed that the product contained 4-(3- and 4-chlorophenyl)pyridines, together with some 4-vinyl pyridine. The data showed that the combined yield of 4-(4-chlorophenyl)pyridine and 4-(3-chlorophenyl)pyridine was about 30 percent, that the ratio of these isomers (4-chlorophenyl: 3-chlorophenyl) was 4:1 and the ratio of the 4-(3- and 4-chlorophenyl)pyridines to 4-vinyl pyridine was about 19:1.

EXAMPLE XVIII

On heating a mixture of 480 mg of 4-(3- and 4-chlorocyclohex-3-enyl)pyridines with 5 percent palladium on carbon at 290° C. for about 30 minutes, the reaction product was found to contain predominantly 4-phenyl pyridine. Thus, under these conditions both dehydrogenation and dechlorination occurred.

EXAMPLE XIX

An attempt was made to aromatize 4-(3- and 4-chlorocyclohex-3-enyl)pyridines (180 mg) in a mixture of 20 mg of 5 percent palladium on carbon, 5 ml of nitrobenzene and one molar equivalent (based on the para-substituted pyridine reactant) of toluene sulfonic acid. Heating of the product for 6 hours at 220° C. under a nitrogen atmosphere yielded a highly complex mixture of products unworthy of further workup.

EXAMPLE XX

When 240 mg of 4-(3- and 4-chlorocyclohex-3-enyl)-pyridines was heated with 30 mg of 5 percent palladium on carbon in 10 ml of a mixture of tetradecene in liquid paraffin at 240° C. for 10 hours, HPLC indicated that the reaction had not proceeded favorably under these conditions.

EXAMPLE XXI

A pressure autoclave equipped with a stirrer, thermocouple and several inlet means was charged with 2 g of 4-(3- and 4-chlorocyclohex-3-enyl)pyridines, 100 mg of 5 percent palladium on carbon and 100 ml of hexadecene. One of the inlets to the autoclave was attached to a source of pressurized ethylene and the autoclave pressurized to 200 psi with ethylene. The sealed autoclave was then heated to 100° C. and kept there for 3 hours. Analysis of a sample of the reaction mixture by HPLC showed that no reaction had occurred. Accordingly, the mixture was heated to 200° C. and kept there for 2 hours. HPLC again indicated that no reaction had occurred. Thereupon, the ethylene pressure was increased to 600 psi and the temperature raised to 300° C. and held there for one hour. In this instance HPLC showed that a small amount of reaction had occurred.

EXAMPLE XXII

A mixture of 0.5 grams of 4-(3- and 4-chlorocyclohex-3-enyl)pyridines, 30 mg of 5 percent palladium on carbon and 20 ml of nitrobenzene was heated in incremental stages. On heating at 100° C. for 2 hours HPLC revealed no reaction had occurred. Heating at 200° C. for 2 hours again produced no reaction. On heating at 250° C. reaction was found to have commenced.

EXAMPLE XXIII

A mixture of 250 mg of 4-(3- and 4-chlorocyclohex-3-enyl)-pyridines, 2 ml of p-cymene and 10 mg of 5 percent palladium on carbon was heated at 177° C. for 10 hours. Analysis of the product mixture by HPLC showed that only a low conversion to reaction products had occurred. The reaction products appeared to be composed of 4-phenyl pyridine and 4-(4- and 3-chlorophenyl)pyridines in approximately equal amounts.

In addition to having the pesticidal properties reported in Netherlands Application No. 6,414,307 [Chemical Abstracts, 64, 713d (1966)], the 4-(4-chlorophenyl)pyridines and 4-(3-chlorophenyl)-pyridines are useful intermediates for the synthesis of other biologically active substances, such as for example 1,4-dihydro-4-oxo-7-(4-pyridyl)-3-quinoline carboxylic acid derivatives which are known to have useful antibacterial properties. Information concerning such derivatives is given in U.S. Pat. Nos. 3,753,993 and 3,907,808, both to Lesher and Carabateas. The novel 4-(3- and 4-chlorocyclohex-3-enyl)pyridines of this invention are likewise useful as intermediates for the synthesis of various biologically active substances, including the foregoing phenyl pyridine pesticides and pyridyl quinoline carboxylic acid type antibacterials.

I claim:
1. In admixture the compounds, 4-(4-chlorocyclohex-3-enyl)pyridine and 4-(3-chlorocyclohex-3-enyl)pyridine.
2. 4-(4-Chlorocyclohex-3-enyl)pyridine.
3. 4-(3-Chlorocyclohex-3-enyl)pyridine.

* * * * *